United States Patent [19]

Dickens

[11] Patent Number: 5,912,360

[45] Date of Patent: Jun. 15, 1999

[54] DIOXOLANE INTERMEDIATES

[75] Inventor: Jonathan Philip Dickens, Cambridge, United Kingdom

[73] Assignee: British Biotech Pharmaceuticals Limited, Oxford, United Kingdom

[21] Appl. No.: 08/956,338

[22] Filed: Oct. 23, 1997

Related U.S. Application Data

[63] Continuation-in-part of application No. 08/374,602, filed as application No. PCT/GB93/01557, Jul. 23, 1992.

[30] Foreign Application Priority Data

Jul. 23, 1992 [GB] United Kingdom ............... 9215665

[51] Int. Cl.[6] .................................................. C07D 317/00
[52] U.S. Cl. ........................................... 549/296; 549/295
[58] Field of Search ................................................ 549/296

[56] References Cited

U.S. PATENT DOCUMENTS

| 4,824,970 | 4/1989 | Castaldi et al. | 549/296 |
| 4,845,243 | 7/1989 | Giordano et al. | 549/296 |
| 5,004,832 | 4/1991 | Castaldi et al. | 562/490 |

OTHER PUBLICATIONS

Calderari et al., "Asymmetric Michael Additions. Stereoselective alkylation of chiral, non–racemic enolates by nitro olefins. Preparation of enatiomerically pure gamma–aminobutyric and succinic acid derivatives", Helv. Chim. Acta 68(6), pp. 1592–1604 and 1985.

*Primary Examiner*—Dwayne C. Jones
*Attorney, Agent, or Firm*—Hale and Dorr LLP

[57] ABSTRACT

The present invention relates to intermediates, useful for the preparation of therapeutically active hydroxamic acid derivatives which are inhibitors of metalloproteinases involved in tissue degradation, and are inhibitors of the release of tumour necrosis factor from cells.

8 Claims, No Drawings

DIOXOLANE INTERMEDIATES

CROSS-REFERENCE TO RELATED APPLICATIONS

This application is a continuation-in-part of U.S. Application Ser. No. 08/374,602, filed Jan. 23, 1995, issued as U.S. Pat. No. 5,700,838, which claims priority under § 371 to PCT/GB93/01557, filed Jul. 23, 1992, which claims priority to Great Britian Application No. 9215665.2 filed Jul. 23, 1992.

FIELD OF THE INVENTION

The present invention relates to intermediates, useful for the preparation of therapeutically active hydroxamic acid derivatives which are inhibitors of metalloproteinases involved in tissue degradation, and are inhibitors of the release of tumour necrosis factor from cells.

SUMMARY OF THE INVENTION

The copending application, U.S. Ser. No. 08/374,602, issued as U.S. Pat. No. 5,700,838, describes and claims compounds of formula (I) which are inhibitors of metalloproteinases involved in tissue degradation, and are inhibitors of the release of tumour necrosis factor from cells:

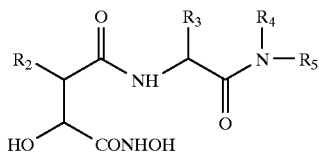

(I)

wherein $R_2$ represents a group $R_6$—A— wherein A represents a divalent straight or branched, saturated or unsaturated hydrocarbon chain of up to 6 C atoms which may be interrupted by an O or S atom, and $R_6$ represents hydrogen or an optionally substituted phenyl, cycloalkyl or cycloalkenyl group;

$R_3$ represents a group $R_7$—(B)$_n$— wherein n is 0 or 1, B represents a divalent straight or branched, saturated or unsaturated hydrocarbon chain of up to 6 C atoms which may be interrupted by an O or S atom, and $R_7$ is —CONHOH, carboxyl, esterified or amidated carboxyl, cycloalkyl, cycloalkenyl, heterocyclyl, phenyl, napthyl, or substituted phenyl or napthyl in which the substituent(s) are selected from phenyl, hydroxy, $C_1$–$C_6$ alkoxy, benzyloxy, trifluoromethyl, halo, or $R^8$—(C=O)—($C_1$–$C_6$alkyl)—O— wherein $R^8$ is hydroxy, amino, or an amino acid residue linked via an amide bond; or (except when n=0) $R_7$ is hydrogen;

$R_4$ represents hydrogen or methyl;

$R_5$ represents hydrogen, $C_1$–$C_6$ alkyl or a group D—($C_1$–$C_6$ alkyl) wherein D represents hydroxy, ($C_1$–$C_6$)alkoxy, ($C_1$–$C_6$)alkylthio, acylamino, optionally substituted phenyl, or a heterocyclic group, $NH_2$, or a mono- or di-($C_1$–$C_6$ alkyl) amine or a heterocyclic group;

or $R_3$ and $R_5$ taken together represent a divalent, saturated or unsaturated hydrocarbon chain of from 8–16 C atoms, which may be interrupted by an O, S or N heteroatom, or a salt, solvate or hydrate thereof, provided that $R_3$ is not the characteristic side chain of a natural alpha-amino acid, or the characteristic side chain of a natural alpha-amino acid in which any functional substituents are protected, any amino groups are acylated, and any carboxyl groups are esterified.

As used herein the term "$C_1$–$C_6$ alkyl" or "saturated hydrocarbon chain of up to 6 C atoms" refers to a straight or branched chain alkyl moiety having from 1 to 6 carbon atoms, including for example, methyl, ethyl, propyl, isopropyl, butyl, t-butyl, pentyl and hexyl.

The term "$C_2$–$C_6$ alkenyl" or "unsaturated hydrocarbon chain of up to 6 C atoms" refers to a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" refers to a saturated alicyclic moiety having from 3-8 carbon atoms and includes, for example, cyclohexyl, cyclooctyl, cycloheptyl, cyclopentyl, cyclobutyl and cyclopropyl.

The term "cycloalkenyl" refers to an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The term "heterocyclyl" or "heterocyclic" refers to a 5–7 membered heterocyclic ring containing one or more heteroatoms selected from S, N and O, and optionally fused to a benzene ring, including for example, pyrolyl, furanyl, thienyl, imidazolyl, oxazolyl, thiazolyl, pyrazolyl, pyridinyl, pyrrolidinyl, pyrimidinyl, morpholinyl, piperizinyl, indolyl and benzimidazole.

Unless otherwise specified in the context in which it occurs, the term "substituted" as applied to any moiety herein means substituted with up to four substituents, each of which independently may be $C_1$–$C_6$ alkoxy, hydroxy, thio, $C_1$–$C_6$ alkylthio, amino, halo (including fluoro, chloro, bromo and iodo), trifluoromethyl, nitro, COOH, —$CONH_2$ or —CONHRA wherein $R^A$ is a $C_1$–$C_6$ alkyl group or the residue of a natural alpha-amino acid.

The term "characteristic side chain of a natural alpha-amino acid" means the characteristic side chain attached to the —CH($NH_2$)(COOH) moiety in the following amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Where a carboxylic acid group is esterified in compounds of formula (I), the notional esterifying moiety may be, for example, a $C_1$–$C_6$ alkanol or benzyl alcohol.

Where a carboxylic acid group is amidated in compounds of formula (I), examples include aminocarbonyl, ($C_1$–$C_6$ alkyl)aminocarbonyl, di($C_1$–$C_6$ alkyl)aminocarbonyl, and benzylaminocarbonyl groups, as well as carboxylic acid groups amidated with an aminocarboxylic acid such as a natural alpha amino acid (eg glycine, alanine etc).

The present invention provides compounds which are useful as intermediates in the synthesis of the foregoing compounds of formula (I).

DETAILED DESCRIPTION OF THE INVENTION

According to the present invention there is provided a compound of formula (V)

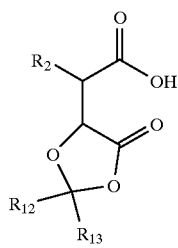

(V)

wherein

R$_2$ represents a group R$_6$—A— wherein A represents a divalent straight or branched, saturated or unsaturated hydrocarbon chain of up to 6 C atoms which may be interrupted by an O or S atom, and R$_6$ represents hydrogen or an optionally substituted phenyl, cycloalkyl or cycloalkenyl group; and the groups R$_{12}$ and R$_{13}$ are hydrogen, alkyl, phenyl or substituted phenyl;

or an activated derivative thereof.

Activated derivatives of the compounds of the invention include the pentafluorophenyl ester, acid anhydrides, or acid halides.

In the compounds of the invention, the C atom carrying the R$_2$ group preferably has R stereochemistry.

In the compounds of the invention R$_2$ may for example be a C$_3$–C$_6$ alkyl, cycloalkyl(C$_3$–C$_6$ alkyl), phenyl(C$_2$–C$_6$ alkyl), C$_2$–C$_4$ alkoxy(C$_1$–C$_3$ alkyl)$_m$, or C$_2$–C$_4$ alkylsulphanyl(C$_1$–C$_3$ alkyl)$_m$ group wherein m is 0 or 1. Examples of particular R$_2$ groups include iso-butyl, n-pentyl, cyclohexylpropyl, cyclohexylbutyl, cyclohexylpentyl, and phenylethyl.

Specific examples of compounds of the invention are:

2R-(2,2-Dimethyl-4-oxo-1,3-dioxalan-5S-yl)-4-methylpentanoic acid, and Pentafluorophenyl 2 R-(2,2-dimethyl-4-oxo-1,3-dioxalan-5S-yl)-4-methyl pentanoate.

Intermediates of the invention are useful for the preparation of compounds of formula (I) above by a process including the step of coupling a compound of formula (V) as defined above, or an activated derivative thereof, with an amine of formula (IV)

(IV)

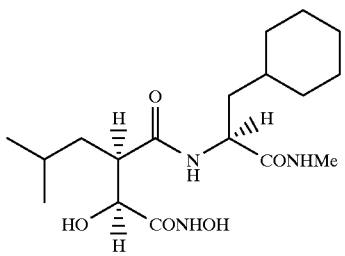

wherein R$_3$, R$_4$, and R$_5$ are as defined in general formula (I) above. The following Example illustrates the use of compounds of the invention in such a process.

EXAMPLE 1

N$^2$-[3S-Hydroxy-4-(N-hydroxyamino)-2R-isobutylsuccinyl]-L-cyclohexyl alanine-N$^1$ methylamide EXAMPLE 1a Isopropyl 3R-carboxyisopropyl-2S-hydroxy-5-methylhex-5-enoate Diisopropyl-2S-hydroxybutanedioate (50 g, 230 mmol) was added to a solution of lithium N,N-diisopropylamide [from N,N-diisopropylamine (80 ml, 570 mmol) and 10M n-butyllithium (48.1 ml, 481 mmol)] in dry tetrahydrofuran (500 ml) whilst maintaining the temperature at −70° C. When addition was complete the reaction was warmed to −15° C. and stirred for 8 hours. The reaction mixture was cooled to −70° C. and methallyl iodide (46 g, 252 mmol) was added slowly, ensuring that the temperature did not exceed −65° C. The mixture was warmed to −40° C. and stirred for 18 hours before quenching at −15° C. with citric acid. The organic layer was separated and washed with 10% sodium bicarbonate solution (500 ml) and brine (300 ml) then dried over magnesium sulphate. The solution was filtered and concentrated in vacuo to give a brown oil (64 g) which was purified by column chromatography (silica gel, 1 kg, gradient elution with 20 to 35% diethyl ether in hexane). The desired product was isolated as a colourless oil (30.9 g, 49%) which was found to be a 17:1 mixture of diastereomers by NMR. $^1$H-NMR; d (Chloroform-d, major diastereomer), 5.06 (1H, septet, J=6.3 Hz), 4.97 (1H, septet, J=6.3 Hz), 4.78 (2H, d, J=7.1 Hz), 4.16 (1H, m), 3.20 (1H, d, J=6.2 Hz), 3.00 (1H, m), 2.50, 2.35 (2H, ABX, J=7.0, 8.7, 14.4 Hz), 1.72 (3H, s) and 1.24–1.16 (12H, 2m).

EXAMPLE 1b

Isopropyl 3R-carboxyisopropyl-2S-hydroxy-5-methylhexanoate

Isopropyl 3R-carboxyisopropyl-2S-hydroxy-5-methylhex-5-enoate (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). $^1$H-NMR; d (Chloroform-d), 5.06 (1H, septet, J=6.3 Hz), 4.97 (1H, septet, J=6.3 Hz), 4.17 (1H, br s,), 3.24 (1H, br s), 2.83 (1H, m), 1.68 (2H, m), 1.44 (1H, m), 1.24 (6H, d, J=6.2 Hz), 1.18 (6H, d, J=6.2 Hz) and 0.89 (6H, m).

EXAMPLE 1c

3R-Carboxy-2S-hydroxy-5-methylhexanoic acid

Isopropyl 3R-Carboxyisopropyl-2S-hydroxy-5-methylhexanoate (7.0 g, 25.6 mmol) was dissolved in dioxane (15 ml) and water (15 ml), a solution of potassium hydroxide (4.29 g) in water (22 ml) was added and the mixture was heated at 90° C. overnight. The solution was allowed to cool and then passed through an ion exchange resin (Dowex [Registered Trade Mark] 50X4-400, 200 ml) to yield the title compound (4.82 g, 99%). $^1$H-NMR; d (Chloroform-d), 8.70 (2H, br s), 4.32 (1H, br s), 3.10 (1H, m), 1.85 - 1.55 (3H, m) and 0.96 (6H, m).

EXAMPLE 1d 2R-(2,2-Dimethyl-4-oxo-1,3-dioxalan-5S-yl)-4-methylpentanoic acid 3R-Carboxy-2S-hydroxy-5-methylhexanoic acid (5.19 g, 27.3 mmol) was dissolved in 2,2-dimethoxypropane (150 ml) and N,N-dimethylformamide (40 ml) and stirred overnight at 30° C. in the presence of a catalytic amount of p-toluene sulphonic acid. The solvent was removed to give the title compound contaminated with solvent (6.87 g, >100%). $^1$H-NMR; d (Chloroform-d), 4.41 (1H, d, J=4.8 Hz), 2.91 (1H, m), 1.69 (3H, m), 1.54 (3H, s), 1.48 (3H, s) and 0.88 (6H, m).

EXAMPLE 1e

Pentafluorophenyl 2R-(2,2-Dimethyl-4-oxo-1,3-dioxalan-5S-yl)-4-methyl pentanoate 2R-(2,2-Dimethyl-4-oxo-1,3-dioxalan-5S-yl)-4-methylpentanoic acid (558 mg, 2.4 mmol) was taken up in dichloromethane (10 ml) and cooled to 0° C. before adding pentafluorophenol (670 mg, 3.6 mmol) and N-ethyl-N'-(3-dimethylaminopropyl) carbodiimide (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). $^1$H-NMR; d (Chloroform-d), 4.57 (1H, d, J=6.5 Hz), 3.32 (1H, m), 1.86 (3H, m), 1.67 (3H, s), 1.58 (3H, s) and 1.03 (6H, m).

EXAMPLE 1f $N^2$-[2R-(2,2-Dimethyl-4-oxo-1,3-dioxalan-5S-yl)-4-methylpentanoyl]-L-cyclohexyl alanine-$N_1$-methylamide Pentafluorophenyl 2R-(2,2-dimethyl-4-oxo-1,3-dioxalan-5S-yl)-4-methyl pentanoate (1.06 g, 2.7 mmol) and L-cyclohexylalanine-N-methylamide (0.33 g, 1.8 mmol) were dissolved in N,N-dimethylformamide (150 ml) and the mixture was stirred overnight at room temperature. The solvent was removed to give an oil which was purified by column chromatography (silica gel, gradient elution with 0 to 5% methanol in dichloromethane) gave first unreacted ester followed by the desired product (0.43 g, 60%). $^1$H-NMR; d (Chloroform-d), 6.47 (2H, br m and d, J=8.3 Hz), 4.53 (1H, d, J=6 Hz), 4.49 (1H, m), 2.76 (4H, m), 1.80–1.50 (12H, br m), 1.62 (3H, s), 1.54 (3H, s), 1.35–1.10 (4H, br m) and 0.91 (6H, m).

EXAMPLE 1g $N^2$-[3S-Hydroxy-4-hydroxy-2R-isobutylsuccinyl]-L-cyclohexylalanine-$N^1$-methylamide.

$N^2$-[2R-(2,2-Dimethyl-4-oxo- 1, 3-dioxalan-5S-yl)-4-methylpentanoyl]-L-cyclohexyl alanine-$N^1$-methylamide (0.43 g, 1.1 mmol) was dissolved in 2M hydrochloric acid (15 ml) and tetrahydrofuran (20 ml) and stirred at room temperature overnight. The solvent was removed to give the required product as an off white foam (0.35 g, 91%). $^1$H-NMR; d (Methanol-$d_4$), 4.37 (1 H, m), 4.16 (1 H, d, J=5.6 Hz), 2.75 (1H, m), 2.68 (3H, s), 1.80–1.50 (12H, m), 1.38–1.10 (4H, m) and 0.90 (6H, m).

EXAMPLE 1h $N^2$-[4-(N-Benzyloxyam ino)-3S-hydroxy-2R-isobutylsuccinyl]-L-cyclohexylalanine-$N^1$-methylamide.

$N^2$-[3S-Hydroxy-4-hydroxy-2R-isobutylsuccinyl)]-L-cyclohexylalanine-$N^1$-methylamide (0.35 g, 1.0 mmol) was taken up in tetrahydrofuran (5 ml) then water (5 ml) and O-benzylhydroxylamine hydrochloride (0.24 g, 1.5 mmol) was added. The solution was cooled to 0° C. before addition of N-ethyl-N'-(3-dimethylaminopropyl) carbodiimide hydrochloride (0.38 g, 2.0 mmol) and the reaction mixture was then stirred at room temperature overnight. Tetrahydrofuran was removed under reduced pressure, whereupon the product crystallised. The mixture was diluted with an equal volume of water and the product was collected by filtration, washed with water and dried under high vaccuum (0.30 g, 65%). $^1$H-NMR; d (Methanol-$d_4$), 7.50–7.30 (5H, m), 4.81 (2H, s; under $H_2O$ peak), 4.36 (1H, t, J=7.6 Hz), 3.98 (1H, d, J=6.1 Hz), 2.72 (1H, m), 2.67 (3H, s), 1.85–1.43 (12H, br m), 1.38–1.10 (4H, br m) and 0.88 (6H, m).

EXAMPLE 1i $N^2$-[3S-Hydroxy-4-(N-hydroxyamino)-2R-isobutylsuccinyl]-L-cylohexylalanine-$N^1$-methylamide.

$N^2$-[4-(N-Benzyloxyamino)-2S-hydroxy-2R-isobutylsuccinyl)]-L-cyclohexylalanine-N'-methylamide (1.0 g, 2.16 mmol) was dissolved in ethanol (100 ml), 10% palladium on charcoal (100 mg) was added and the mixture was subjected to an atmosphere of hydrogen. After 4 hours the catalyst was filtered off then the solvent removed to give the title compound (650 mg, 1.75 mmol, 81%): $^1$H-NMR; d (Methanol-$d_4$), 4.35 (1H, t, J=7.6 Hz), 3.99 (1H, d, J=6.4 Hz), 2.69 (4H, m and s), 1.80–1.50 (12H, br m), 1.40–1.10 (4H, br m) and 0.89 (6H, m). $^{13}$C-NMR; d (Methanol-$d_4$), 175.6, 175.3, 171.5, 72.9, 52.4, 40.2, 39.2, 35.2, 34.9, 33.2, 30.9, 27.6, 27.4, 27.1, 26.9, 26.3, 23.7 and 22.1. Found: C, 58.27, H, 8.93, N, 11.20%; $C_{18}H_{33}N_3O_5$ requires: C, 58.20, H, 8.95, N, 11.31%.

What is claimed:

1. A compound of formula (V):

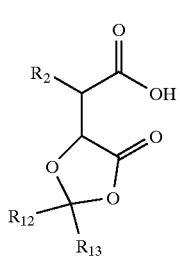

(V)

wherein $R_2$ represents a group $R_6$—A— wherein A represents a divalent straight or branched, saturated or unsaturated hydrocarbon chain of up to 6 C atoms which may be interrupted by an O or S atom, and $R_6$ represents hydrogen or an optionally substituted phenyl, cycloalkyl or cycloalkenyl group; and the groups $R_{12}$ and $R_{13}$ are hydrogen, alkyl, phenyl or substituted phenyl;

or an activated derivative thereof.

2. An activated derivative as claimed in claim 1 which is a pentafluorophenyl ester, acid anhydride, or acid halide.

3. A compound as claimed in claim 1 or claim 2 wherein the C atom carrying the $R_2$ group has R stereochemistry.

4. A compound as claimed in claim 1 or claim 2 wherein $R_2$ represents $C_3$–$C_6$ alkyl, cycloalkyl($C_3$–$C_6$ alkyl), phenyl ($C_2$–$C_6$ alkyls), $C_2$–$C_4$ alkoxy($C_1$–$C_3$ alkyl)$_m$, or $C_2$–$C_4$ alkylsulphanyl($C_1$–$C_3$ alkyl)$_m$ group where m is 0 or 1.

5. A compound as claimed in claim 4 wherein $R_2$ represents n-pentyl, cyclohexylpropyl, cyclohexylbutyl, cyclohexylpentyl, phenylethyl, phenylpropyl, phenylbutyl, phenylpentyl, propyloxymethyl, or propylsulphanyl.

6. A compound as claimed in claim 4 wherein $R_2$ represents isobutyl.

7. 2R-(2,2-Dimethyl-4-oxo- 1,3-dioxalan-5S-yl)-4-methylpentanoic acid.

8. Pentafluorophenyl 2R-(2,2-dimethyl-4-oxo-1,3-dioxalan-5S-yl)-4-methyl pentanoate.

* * * * *